United States Patent [19]

Schwan

[11] 4,044,008

[45] Aug. 23, 1977

[54] 1-[2-HYDROXY-3-(2-NAPHTHOXY)-PROPYL]-2(1H)PYRIMIDONE HYDROCHLORIDE

[75] Inventor: Thomas J. Schwan, Norwich, N.Y.

[73] Assignee: Morton-Norwich Products, Inc., Norwich, N.Y.

[21] Appl. No.: 730,195

[22] Filed: Oct. 6, 1976

[51] Int. Cl.² ........................................ C07D 239/10
[52] U.S. Cl. ................................. 260/251 R; 424/251
[58] Field of Search ................................... 260/251 R

[56] References Cited

U.S. PATENT DOCUMENTS 4,002,626   1/1977   Schwan ..................... 260/251 R Primary Examiner—Donald G. Daus
Assistant Examiner—Jose Tovar
Attorney, Agent, or Firm—Anthony J. Franze

[57] ABSTRACT

1-[2-Hydroxy-3-(2-naphthoxy)propyl]-2(1H)pyrimidone possesses pharmacological activity as a parasympatholytic agent.

2 Claims, No Drawings

1-[2-HYDROXY-3-(2-NAPHTHOXY)PROPYL]-2(1H)PYRIMIDONE HYDROCHLORIDE

This invention relates to the compound of the formula:

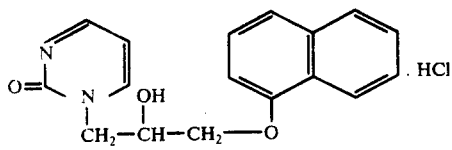

When administered intraperitoneally to animals this compound exhibits parasympatholytic activity. Administration of 50 mg/kg of this compound to anesthetized dogs resulted in a reduction in response to acetylcholine over a duration of 90 minutes.

In order that this invention be readily available to and understood by those skilled in the art the following illustrative example is included: 1-[2-Hydroxy-3-(2-naphthoxy)propyl]-2(1H)pyrimidone hydrochloride.

2-Hydroxypyrimidine hydrochloride (39.9 g, 0.3 mole) in 720 ml of methanol was treated with sodium carbonate (63.6 g, 0.6 mole) followed by a solution of 3-chloro-1-(α-naphthoxy)-2-propanol (71 g, 0.3 mole) and sodium iodide (23 g, 0.15 mole) in 150 ml methanol. The suspension was refluxed for 24 hrs. and then concentrated to dryness in vacuo. The residue was boiled in 500 ml acetonitrile, filtered while hot, and the filtrate cooled to give 37 g (41%) of the free base.

The hydrochloride was prepared by dissolving the free base in the minimum amount of methanol and treating the solution with methanolic hydrogen chloride.

An analytical sample, m.p. 199°, was recrystallized from methanolethyl acetate.

Anal. Calcd. for $C_{17}H_{16}N_2O_3 \cdot HCl$: C, 61.35; H, 5.15; N, 8.42 Found: C, 61.16; H, 5.19; N, 8.35

What is claimed is:

1. A compound of the formula:

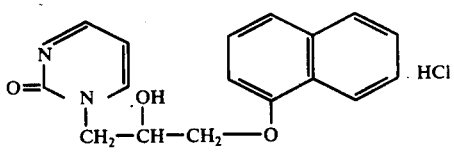

2. A process for the preparation of the compound of claim 1 which consists of reaction of 2-hydroxypyrimidine hydrochloride with 3-chloro-1-(α-naphthoxy)-2-propanol in the presence of sodium carbonate and sodium iodide and reaction of the resulting free base with hydrogen chloride.

* * * * *